US007308106B2

(12) United States Patent
Vaudrey et al.

(10) Patent No.: US 7,308,106 B2

(45) Date of Patent: Dec. 11, 2007

(54) SYSTEM AND METHOD FOR OPTIMIZED ACTIVE CONTROLLER DESIGN IN AN ANR SYSTEM

(75) Inventors: Michael A. Vaudrey, Blacksburg, VA (US); William R. Saunders, Blacksburg, VA (US); Andre Goldstein, Blacksburg, VA (US); William T. Baumann, Blacksburg, VA (US)

(73) Assignee: Adaptive Technologies, Inc., Blacksburg, VA (US)

( * ) Notice: Subject to any disclaimer, the term of this patent is extended or adjusted under 35 U.S.C. 154(b) by 371 days.

(21) Appl. No.: 10/847,171

(22) Filed: May 17, 2004

(65) Prior Publication Data

US 2005/0254665 A1 Nov. 17, 2005

(51) Int. Cl.
*A61F 3/02* (2006.01)

(52) U.S. Cl. .......................................................... 381/72

(58) Field of Classification Search ...... 381/71.1–71.6, 381/72, 71, 94.1–94.9, 93, 95–96
See application file for complete search history.

(56) References Cited

U.S. PATENT DOCUMENTS 5,251,263 A * 10/1993 Andrea et al. ............. 381/71.6
5,600,729 A 2/1997 Darlington et al.
5,711,308 A * 1/1998 Singer ........................ 600/559
5,852,667 A * 12/1998 Pan et al. .................. 381/71.1
6,078,672 A * 6/2000 Saunders et al. .......... 381/71.6
6,396,930 B1 * 5/2002 Vaudrey et al. ............... 381/60
6,449,369 B1 * 9/2002 Carme et al. ............ 381/71.12
6,665,410 B1 12/2003 Parkins
6,829,361 B2 * 12/2004 Aarts ......................... 381/309
6,996,241 B2 * 2/2006 Ray et al. ................ 381/71.11
2002/0076059 A1 * 6/2002 Joynes ...................... 381/71.6
2003/0068048 A1 * 4/2003 Aarts et al. ................ 381/71.6
2004/0086138 A1 * 5/2004 Kuth ........................... 381/72

* cited by examiner

*Primary Examiner*—Vivian Chin
*Assistant Examiner*—Lao Lun-See
(74) *Attorney, Agent, or Firm*—Roberts, Mardula & Wertheim, LLC

(57) ABSTRACT

A tailored active noise control design method is presented that provides for improved noise attenuation performance for each individual user and improved hearing protection in a specified noise field as a function of a specified metric indicative of a noise reduction objection. Characteristics of individual users, behavior of the associated passive hearing protection, and the external noise environment are all concurrently accounted for in an automatic method for designing an active controller that limits the exposed noise level for a specific individual. The controller manufacturing process and implementation may be performed in-situ for each individual automatically. The design method may also account for actuator limitations and can be applied equally well to any passive/active noise control devices including headphones and earplugs.

10 Claims, 10 Drawing Sheets

Disturbance, A-wtd Disturbance, A-wtd Passive Controlled Disturbance

Prior Art Active Control Design, Proposed Active Control Design

A-wtd Passive Controlled Disturbance, Prior Art Perf (97.3dBA), Proposed Performance (92.5dBA)

SYSTEM AND METHOD FOR OPTIMIZED ACTIVE CONTROLLER DESIGN IN AN ANR SYSTEM

BACKGROUND

Embodiments of the present invention relate generally to active noise reduction systems. More specifically, embodiments of the present invention related to an optimized controller for use with active hearing protection devices.

Prolonged or high levels of sound exposure can induce hearing loss. A significant amount of prior research correlates overall A-weighted sound pressure levels with hearing loss metrics. Accordingly, the Occupational Safety and Health Administration guidelines state that by reducing the A-weighted sound pressure level (SPL) at a person's ear, safe exposure time limits may be increased and hearing health may be better preserved. The overall A-weighted level of a sound field is computed as a linear sound power sum over the audible frequency band, where the highest spectral levels will most influence the value of the overall sum. Therefore, hearing protection performance that targets the highest A-weighted levels first will be most effective. If all A-weighted octave band levels are the same, targeting most bands equally is needed to significantly impact the overall A-weighted SPL at the ear, and thus improve the hearing protection performance.

A multitude of hearing protection devices (HPD's) exist that are designed to limit the noise exposure at a person's ear. Both passive and active noise reduction devices are available on the commercial market including headsets, circumaural hearing protectors, and earplugs. Passive hearing protectors often gauge their effectiveness using a noise reduction rating (NRR) which predicts hearing protection performance in a flat broadband noise field. This is a broad ranging metric that indicates general protection in large number of different noise fields but it is not intended to represent optimized noise attenuation for any specific noise field or user.

The usual goal of commercial passive hearing protector designs is to achieve the highest NRR. However, this is not always a good indicator of the performance of the hearing protector compared to other protectors, or compared to the best design possible for a specific noise field that may be different from the pink noise used in the NRR calculation. Since hearing protectors using active noise control (ANC) are not typically evaluated even with the NRR, ANC designs are usually even less correlated with hearing protection performance than are passive designs. The prior art design criteria are primarily concerned with achieving high attenuation over a bandwidth determined by the open loop plant (i.e. the controller in series with the acoustic dynamics of the hearing protector) as well as the desire for a low complexity controller, rather than a consideration of A-weight noise field where the protector will be used.

Besides the lack of correlation between prior art ANC HPD's and reduction of A-weighted noise metrics, there are also deficiencies relative to the optimized performance of ANC HPD's for an arbitrary user. The primary reason for sub-optimal ANC HPD performance is related to the widely varying acoustic frequency response functions measured on an inter-person and even intra-person basis. The variations have resulted in ANC HPD's that emphasize robust closed-loop stability over optimal performance.

Typically, the compromise for ANC circumaural headsets is to rely on a large cup volume so that the acoustic mobility of the ear canal dynamics is not important relative to the acoustic mobility of the earcup's dynamics. Thus, the earcup design is selected to reduce inter-person variations. It is even possible to create intentional holes in the earcup volume to further improve the problem of plant variation from user to user. All of these approaches move away from ANC designs that yield optimal performance based on the actual acoustic frequency response for any particular user.

Prior art ANC earplug styles of HPD's have achieved robust performance through passive design of the acoustic plant to ensure that the earplug's acoustic frequency response (from speaker to microphone) is higher compliance than the ear canal compliance. This can only be achieved by relatively large volumes of space around the feedback microphone and therefore, must be accomplished at locations relatively far from the user's tympanic membrane. However, the distance between the feedback microphone and the tympanic membrane is directly correlated with the bandwidth of ANC that is effective at the tympanic membrane, where farther distances reduce the effective ANC bandwidth for the user. (See "Electronic Earplug For Monitoring And Reducing Wideband Noise At The Tympanic Membrane" U.S. application Ser. No. 10/440,619, which is incorporated herein by reference in its entirety for all purposes). Where variations in the open loop frequency response are designed away passively, as in using additional acoustic volume, optimal performance is sacrificed.

Attempts have been made to improve controller designs to account for additional variables. U.S. Pat. No. 6,665,410 issued to Parkins describes an active noise controller design approach that achieves the same performance for all individuals by altering the controller design to accommodate changes in the plant (the dynamics associated with the actuator, sensor, and acoustic dynamics in the occluded space). The controller is adjusted to produce a specified open loop response (controller in series with the plant). However, using a target open loop performance assures that some members of the user population will have plants that do not permit a realizable controller to achieve the target while other members will have plants that result in sub-optimum performance by application of the target. Ultimately, the optimal open loop shape varies from person to person and by designing the controller to achieve a fixed loop shape, almost all people will either not be able to attain the target design, or will not achieve optimal performance.

U.S. Pat. No. 5,600,729 issued to Darlington et. al. presents an adaptive feedback control technique that designs a controller in real time to minimize a noise impinging on a microphone. The configuration of the adaptive controller in the feedback loop can lead to instability for an arbitrarily small error in the plant identification required by the design process. Such a design is practically problematic since stability of the closed loop system during operation is not assured. In addition, Darlington does not specify a metric associated with hearing protection that is to be minimized.

Because the plant and passive control can change from person to person, a generalized controller design will actually be sub-optimal for all individuals. A fixed active controller design commonly applied to ANR hearing protection systems is a generic system that does not utilize any specific information about the user or noise field in which it operates. Such a static controller design that does not take into account any noise field characteristics, any passive control characteristics, any A-weighting or hearing protection weighting, or any plant dynamic characteristics that change from person to person, will result in hearing protection performance that is not the best achievable from that particular situation.

What is needed is an active noise controller that includes all of the necessary design variables to ensure the maximum available performance for every individual. Such a controller would achieve the best possible performance for each user by designing a unique controller to automatically maximize performance.

SUMMARY

In an embodiment of the present invention, a sound reduction device comprises means for passively reducing the sound pressure proximate to the ear canal of a user, a sound sensor, an actuator and a controller implemented on a controller processor. A computing platform is adapted to determine a transfer function "H" to provide active noise reduction tailored to the user of the sound reduction device based on minimizing a metric indicative of a noise reduction objective. The transfer function "H" is determined using an optimizing controller design system (OCDS). The OCDS determines appropriate parameters for incorporation into the particular controller processor to be used to implement the transfer function "H" produced by the OCDS.

The OCDS accounts for plant variation among individuals, variations in passive noise control performance of the hearing protector device, the external noise spectrum to be controlled, and a performance metric associated with a noise reduction objective. The OCDS incorporates information about the ambient noise field, the passive performance of the hearing protector, and the personal acoustic dynamic system of the target individual to minimize the performance metric associated with a noise reduction objective.

It is therefore an aspect of the present invention to customize a controller design for an active noise reduction (ANR) hearing protection system (HPS) for each user of that system taking into account the passive noise reduction of the system, the user's "plant," and the environment in which the system will be used.

It is another aspect of the present invention to minimize a controller design metric so as to provide effective active control hearing protection performance delivered under a passive hearing protector.

It is yet another aspect of the present invention to accommodate the physiological characteristics of a user of an ANR HPS while optimizing the hearing protection afforded that user for any specific passive protector design ranging from circumaural earcups to deep-insert custom earmolds.

It is still another aspect of the present invention to modify a controller design metric to include a penalty factor in the controller design procedure in order to protect the active control actuator from damage.

It is another aspect of the present invention to include in the active control design, the passive control performance and the ambient noise field to ensure that the best overall hearing protection performance is achieved through the automatic design of a controller transfer function and implementation of the transfer function in the controller processor.

It is yet another aspect of the present invention to provide an active controller design method that automatically produces an optimal controller architecture depending on the user, the passive hearing protection performance, the noise field, and the actuator dynamics to provide hearing protection that is based on the dB(A) metric associated with effective hearing protection.

In an embodiment of the present invention, a sound reduction device comprises means for passively reducing the sound pressure proximate to the ear canal of a user, a sound sensor, an actuator; a computing platform, and a controller processor. The computing platform is adapted to determine a transfer function "H" to provide active noise reduction tailored to the user of the sound reduction device based on minimizing a metric indicative of a noise reduction objective. The sound reduction device may be a circumaural earcup protector, a custom earplug protector, or a generic-fit earplug protector. In another embodiment of the present invention, the metric indicative of a noise reduction objective utilizes a calculation of an amplitude-weighted sound pressure level using the actuator. The controller processor is adapted to implement the transfer function "H." The controller processor may be a digital filter, an analog filter, or a filter using both analog and digital signal processing means. In still another embodiment of the present invention, the metric indicative of a noise reduction objective utilizes a calculation of a perceived loudness using the actuator. In yet another embodiment of the present invention, the metric indicative of a noise reduction objective comprises a metric indicative of hearing protection.

In another embodiment of the present invention, a sound reduction device comprises a computing platform, wherein in response to a configuration signal the computing platform is adapted to determine a transfer function "H" to provide active noise reduction tailored to the user of the sound reduction device based on minimizing a metric indicative of a noise reduction objective. The configuration signal may be a signal indicative of a first use of the sound reduction device, a signal indicative of a time, a signal indicative of an elapsed time, a signal indicative of a request by the user of the sound reduction device, a signal indicative of a change in an external noise field in which the sound reduction device was last used; a signal indicative of a change in the actuator dynamics, and a signal indicative of a change in an acoustic response of a space enclosed by the sound reduction device.

In an alternate embodiment of the present invention, a sound reduction device comprises means for passively reducing the sound pressure proximate to the ear canal of a user, a sound sensor, an actuator; a computing platform, and a controller processor. The computing platform is adapted to receive an ambient noise field "N" over a spectral segment, select a design metric "M" indicative of a noise reduction objective, receive a measure of the passive performance "P" of the hearing protection device, determine a measure of the acoustic dynamic response "G" of the user of the hearing protection device to a control signal; and determine a transfer function "H" for a controller based on "N", "P", "M", and "G". Additionally, the computing platform is adapted to optimize the transfer function "H" using a least-squares solution, a gradient descent optimization solution, a convex surface optimization solution, or a time-averaged gradient method. The controller processor is adapted to implement the transfer function "H." The controller processor may be a digital filter, an analog filter, or a filter using both analog and digital signal processing means.

In another embodiment of the present invention, the computing platform is further adapted to apply a cost function to determine an optimal transfer function "$H_O$" that minimizes the average power of the design metric "M" when applying "N", "P", and "G". Optionally, the cost function comprises an actuator signal penalty to limit damaging signals to the actuator. The sound reduction device may be a circumaural earcup protector, a custom earplug protector, or a generic-fit earplug protector.

In another embodiment of the present invention, the metric indicative of a noise reduction objective utilizes a calculation of an amplitude-weighted sound pressure level using the actuator. In still another embodiment of the present invention, the metric indicative of a noise reduction objective utilizes a calculation of a perceived loudness using the actuator. In yet another embodiment of the present invention, the metric indicative of a noise reduction objective comprises a metric indicative of hearing protection.

The present invention further provides a process for designing an optimized active noise suppression controller. An ambient noise field "N" is determined over a spectral segment. In an embodiment of the present invention, the ambient noise field "N" is selected from a library of noise fields. A design metric is selected that is indicative of a noise reduction objective of a noise reduction device. In an embodiment of the present invention, the design metric may be a calculation of the amplitude-weighted sound pressure level, a C-weighted sound pressure level, or loudness. In another embodiment of the present invention, a design metric indicative of hearing protection is selected. In still another embodiment of the present invention, the design metric indicative of a noise reduction objective is selected from a library of design metrics. A measure of the passive performance "P" of the noise reduction device is determined as is a measure of the acoustic dynamic response "G" of a user of the noise reduction device to a control signal. A transfer function "H" for a controller based on "N", "P" and "G" is determined.

The process of the present invention further provides for optimizing the transfer function "H" by applying a cost function to determine an optimal transfer function "H" that minimizes the average power of the design metric "M" when applying "N", "P", and "G". Optionally, the cost function comprises an actuator signal penalty to limit damaging signals to the actuator.

Embodiments of the present invention provide for a configurable controller made by the process previously described. In an another embodiment of the present invention, the configurable controller comprises means for determining whether a change has occurred in an ambient noise field "N" over a spectral segment used to determine the transfer function "H", means for determining whether a change has occurred in a measure of the passive performance "P" of a hearing protection device used to determine the transfer function "H", and means for determining whether a change has occurred in a measure of the acoustic dynamic response "G" of a user of the hearing protection device to a control signal used to determine the transfer function "H". In the event a change is detected in any one of N, P, and G, the configurable controller applies means for producing a revised transfer function "$H_R$" according to a process previously described, and means in the controller processor for implementing transfer function "$H_R$".

In still another embodiment of the present invention, the configurable controller also comprises means for selecting a design metric indicative of a noise reduction objective and means for determining whether the selected design metric differs from the design metric used to determine the transfer function "H". In the event the selected design metric differs from the from the design metric used to determine the transfer function "H", the configurable controller applies means for producing a revised transfer function "H"$_R$ according to a process previously describe, and means in the controller processor for implementing transfer function "$H_R$".

DETAILED DESCRIPTION

In an embodiment of the present invention, a sound reduction device comprises means for passively reducing the sound pressure proximate to the ear canal of a user, a sound sensor, an actuator and a controller implemented on a controller processor. A computing platform is adapted to determine a transfer function "H" to provide active noise reduction tailored to the user of the sound reduction device based on minimizing a metric indicative of a noise reduction objective. The transfer function "H" is determined using an optimizing controller design system (OCDS). The OCDS determines appropriate parameters for incorporation into the particular controller processor to be used to implement the transfer function "H" produced by the OCDS.

The OCDS automatically accounts for plant variation among individuals, variations in passive noise control performance of the hearing protector device, the external noise spectrum to be controlled, and a performance metric associated with a noise reduction objective. The OCDS incorporates information about the ambient noise field, the passive performance of the hearing protector, and the personal acoustic dynamic system of the target individual to minimize the performance metric associated with a noise reduction objective. There are several criteria that must be taken into account when considering active control design for optimized hearing protection performance including: anatomy and physiology, electronic system variations, passive hearing protector performance, and perhaps most importantly the shape of the disturbance noise field that the exposed user resides in. In an embodiment of the present invention, a control design process results in a hearing protector system designed specifically for improving hearing protection through an optimizing and integrated design procedure.

Figure 1:
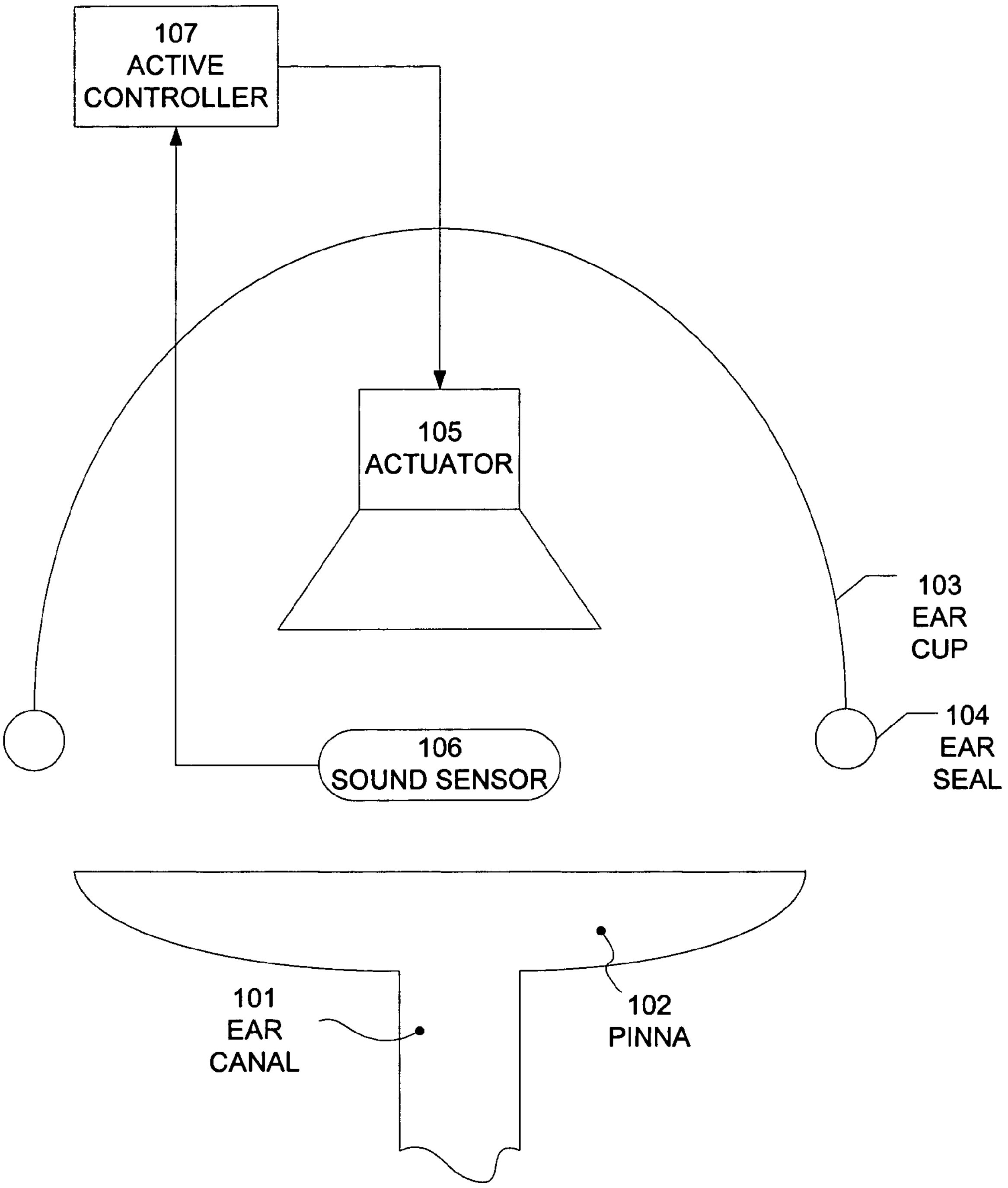
FIGURE 1 PRIOR ART
FIG. 1 illustrates a passive/active noise control headset design known in the prior art.
Figure 2:
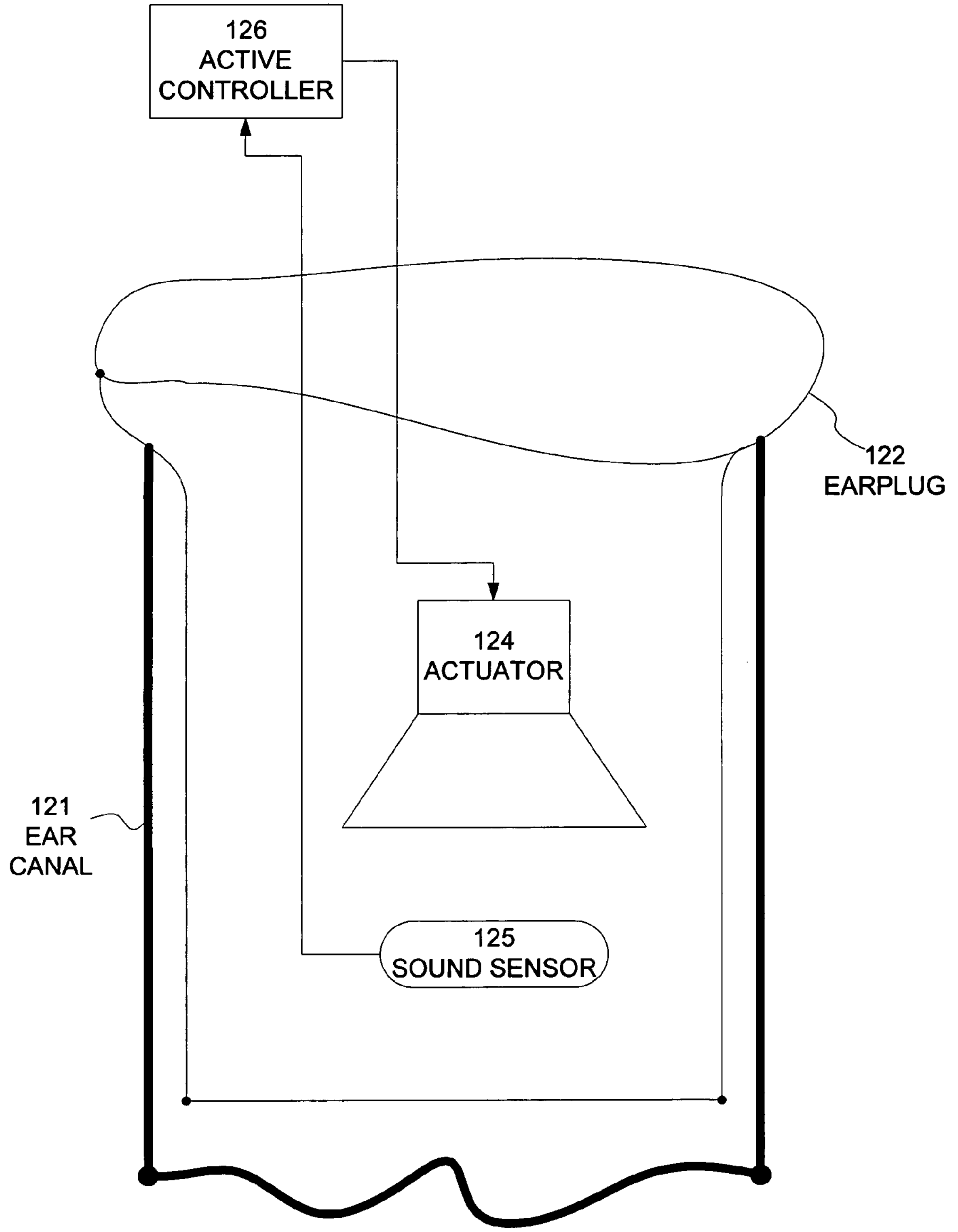
FIGURE 2 PRIOR ART
FIG. 2 illustrates a passive/active earplug design know in the prior art.

FIGS. 1 and 2 illustrate two types of hearing protector designs known in the art each incorporating active noise reduction. FIG. 1 illustrates a passive/active noise control headset design known in the prior art. The ear canal 101 and pinna 102 are enclosed by an ear cup 103 and ear seal 104. The ear cup and ear seal provide passive attenuation between the ambient noise and the wearer's ear canal because no active components are required. This is sometimes referred to as an "insertion loss." The amount of passive attenuation is a function of the hearing protector design and seal effectiveness and can be tested in a variety of known ways including microphone in real ear (MIRE ANSI standard S12.42) and real ear attenuation at threshold (REAT ANSI standard S12.6). In addition to passive control, active noise reduction may be employed to provide additional sound attenuation to the ear canal. For known feedback control systems this involves a speaker (or actuator) 105, a microphone (or sound sensor) 106 and a controller 107.

FIG. 2 illustrates a passive/active earplug design known in the prior art. Here an earplug 122 is used as the passive hearing protector and is inserted into the ear canal 121. The active control components (speaker or actuator 124 and microphone or sound sensor 125) are housed inside the earplug and are controlled by the active controller 126. For earplug designs, the passive control is typically measured using only the REAT attenuation method. However, a more quantitative measure of the insertion loss can be conducted by using the microphone 125 to measure either the difference in the ambient noise and the noise measured inside the occluded earplug or by simply measuring the calibrated spectrum inside the occluded earplug that corresponds generally to the spectrum inside the ear canal 121 over a large frequency band. The physical device of FIG. 2 may also be accompanied by a passive circumaural hearing protector that surrounds the ear much like that which is depicted in FIG. 1. Such a device may or may not also have active control, but will contribute at least some amount of additional passive attenuation to the ear canal location.

While embodiments of the present invention may be utilized in conjunction with the reduction devices illustrated in FIGS. 1 and 2, the present invention is not so limited. As will be appreciated by those skilled in the art, systems and methods of the present invention may be applied to any active sound reduction device without departing from the scope of the present invention.

Figure 3:
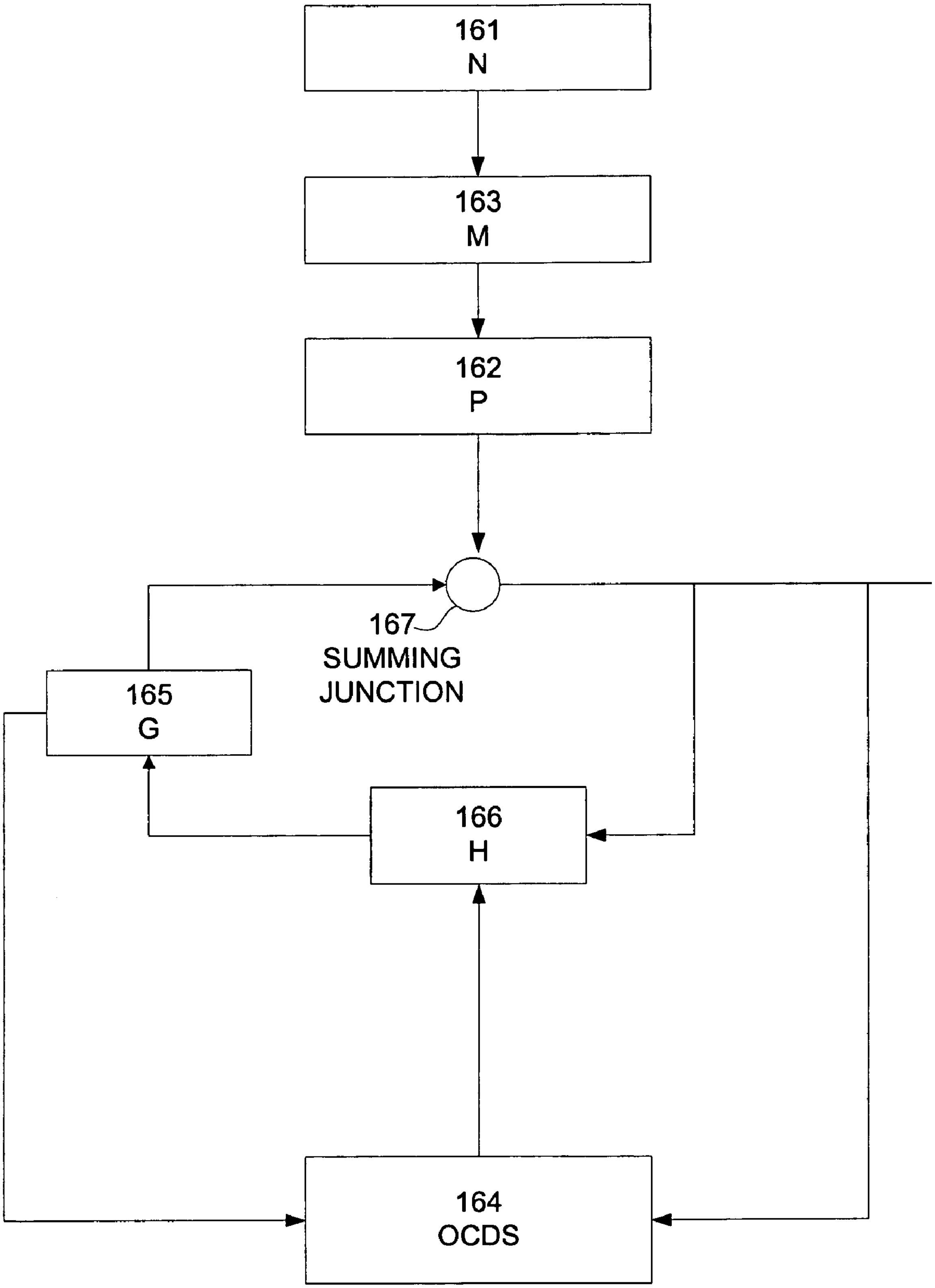
FIG. 3 illustrates the logical components of an optimized controller design system (OCDS) according to embodiments of the present invention.

FIG. 3 illustrates the logical components of an optimized controller design system (OCDS) according to embodiments of the present invention. Referring to FIG. 3, the transfer function "H" 166 is associated with active controller 107 and 126 of FIG. 1 or 2 (depending on the type of sound reduction device used). The dynamics associated with the actuator, sensor, and acoustic dynamics in the occluded space are represented in FIG. 3 by G 165, also commonly referred to as the "plant." Information about the environment, the user's plant, and passive hearing protector are used by the OCDS 164 to produce a controller design that minimizes a controller design metric indicative of improved hearing protection. By way of illustration and not as a limitation, in one embodiment the controller design metric is the A-weighted sound pressure level (SPL) measured as dB(A). As will be appreciated by those skilled in the art, other controller design metrics may be used by an OCDS without departing from the scope of the present invention. For example, in another embodiment of the present invention, the controller design metric is dB(C). In yet another embodiment of the present invention the controller design metric is perceived loudness. The controller design that results from the application of the OCDS may be used in conjunction with any hearing protector designs known in the art, including those illustrated in FIGS. 1 and 2.

In an alternate embodiment of this invention, the sound sensor or microphone described above may be a sensor that monitors the velocity of the tympanic membrane. This may be accomplished using a non-contact laser vibrometer, or accelerometer placed directly on the tympanic membrane. In this embodiment, the controller design metric is the velocity of the eardrum.

Referring again to FIG. 3, a flat, broadband noise input "n" is shaped in magnitude by N 161. N represents the shape of the ambient disturbance noise amplitude spectrum to be attenuated. This is completely dependent on the spectral content of the noise field that is to be controlled. The resulting waveform is applied to M 163 and shaped according to the controller design metric used by the OCDS. In an embodiment of the present invention, this is the dB(A) amplitude weighted sound pressure level (A-weighted SPL). It should be noted that it is also equivalent to include the weighting M 163 as an output weighting on the signal e prior to its inclusion in the control design procedure.

In an alternate embodiment of the present invention, the controller design metric is "loudness". Loudness more accurately represents the human perception of the level of ambient noise. Loudness is appropriate in circumstances where hearing protection is not the primary concern. Under these circumstances, the resulting controller design will minimize loudness instead of the A-weighted SPL. Whether it is the dB(A), dB(C), loudness, or other metric, it is included in the formulation of the controller design as M 163 in FIG. 3.

After being filtered by the weighting shapes in N and M, the signal is shaped further with P 162. P 162 represents the passive noise attenuation of the specific hearing protector that contains the active control plant. By way of illustration, the hearing protector may be the headset illustrated in FIG. 1, the earplug illustrated in FIG. 2, or it may be an earplug in addition to a headset. Each of these hearing protectors has different design variables that govern the amount of passive attenuation that is afforded by that hearing protector. The passive attenuation of a device will also vary depending on the user wearing that device. The type of passive device therefore impacts the spectral content of the noise reaching the user's ear canal located at approximately the summing junction 167.

P 162 can be determined for each individual because the hearing protection performance will vary as a function of user fit. Alternatively, a passive hearing protector may be tested in advance to obtain its average attenuation performance. P 162 may, therefore, represent the average, the specific performance, or some conservative estimate that may include standard deviation from prior measurements.

As a result of filtering a signal ("n") with N 161, M 163, and P 162, an accurate, personalized, and tailored representation of the noise at the user's ear is achieved.

Figure 6:
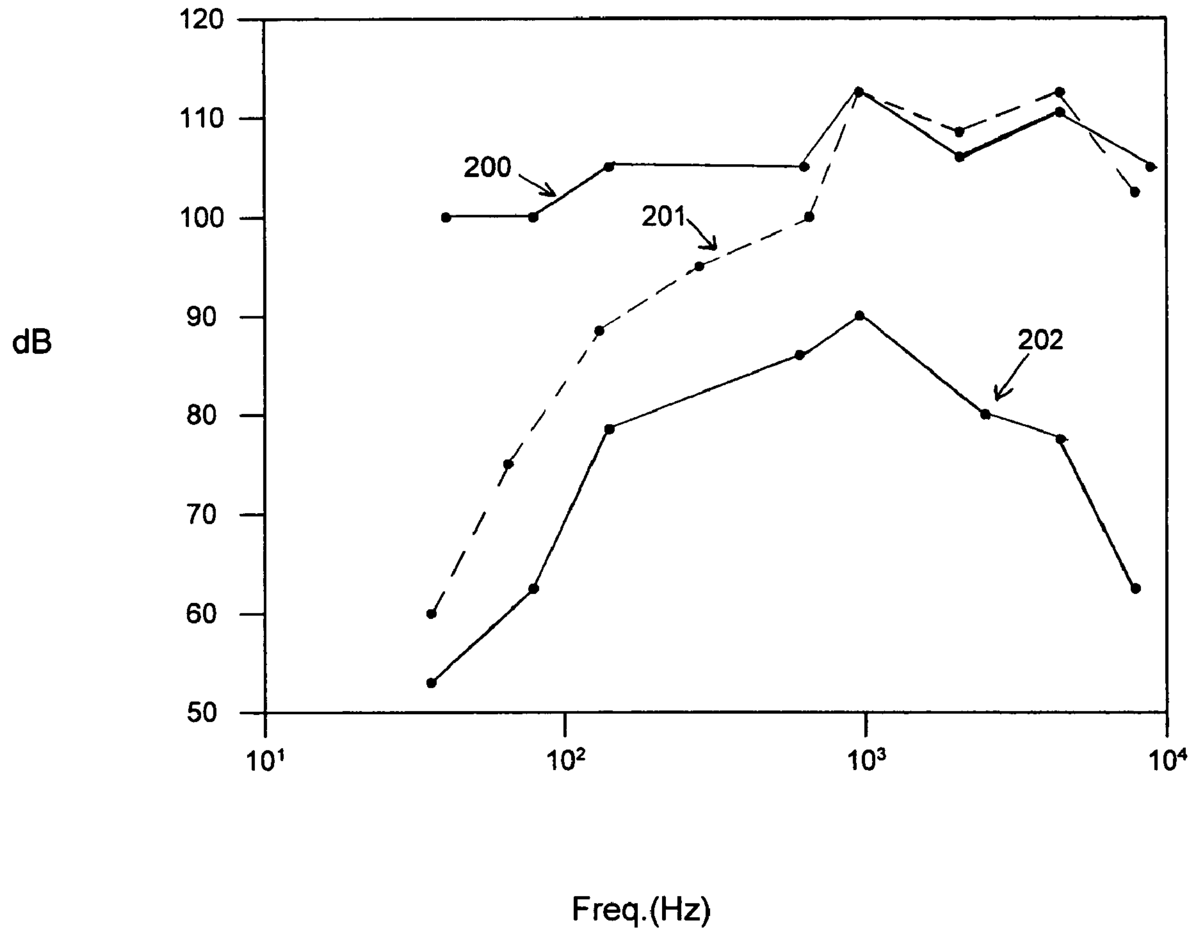
FIG. 6 spectra of signals involved in the optimized controller design process according to embodiments of the present invention.

FIG. 6 illustrates spectra of signals involved in the optimized controller design process according to embodiments of the present invention. The signal n begins as a flat broadband signal. The first shaping or filtering is by N 161 and is represented by spectrum 200. Because n is flat, the filtered spectrum of n results in the spectrum 200. This is an example of a relatively broadband noise field that may require both passive and active control. Next the metric based filtering M 163 (here A-weighting) is applied to the disturbance-filtered spectrum to result in spectrum 201. (The A-weighting de-emphasizes low frequencies below 1 kHz and is highly correlated with exposure-related hearing loss). The passive hearing protector weighting P 162 is then applied and the filtered result is shown as spectrum 202. The difference between traces 201 and 202 represents the passive hearing protection performance of the example presented here. Note that this performance is different for every hearing protector and person, and must be included for the individual control design technique to be effective. The resulting trace, 202, represents the spectrum that the user will be exposed to when in that specific noise field, under that specific hearing protector, and weighted to emphasize only the frequencies that will contribute to hearing loss. Therefore, this spectrum is not necessarily the actual power spectrum of the noise at the ear canal, but instead more accurately represents the exposure danger that the individual is subject to. It is this spectrum that the OCDS 164 seeks to modify in order to improve hearing protection performance.

Referring again to FIG. 3, the OCDS 164 in FIG. 3 incorporates all information from the individual's plant G 165, the metric based performance M 163, the noise field and weighting N 161, and the passive control performance P 162 to produce the transfer function "H" 166. The OCDS 164 will minimize the chosen metric M 163 given all of these parameters. Because the metric is minimized, no specific target performance is indicated. This means that each individual and each noise field will receive the best possible customized and tailored performance based on the metric that is being minimized. Thus, the OCDS 164 avoids the inefficiencies associated with generic target design systems in which the resulting controller design is either under designed or not practically achievable.

The signal e can be described by the following expression:

$$e = \left[\frac{NMP}{1 + GH}\right]n$$

In an embodiment of the present invention, an OCDS 164 determines the optimal solution for transfer function "H" 166 by minimizing a cost function of the form:

$$J=E[e^T e].$$

The signal e represents the shaped signal whose average power J is equivalent to the chosen metric M for the user's plant G in the noise field N and passive control P. The minimum achievable cost will vary with changes in G, N, M, or P. With the given parameters, the controller can be designed to minimize the cost J in a variety of ways. By way of illustration and not as a limitation, one effective technique for designing such a controller is known as the Linear Quadratic Gaussian (LQG) technique.

Figure 9:
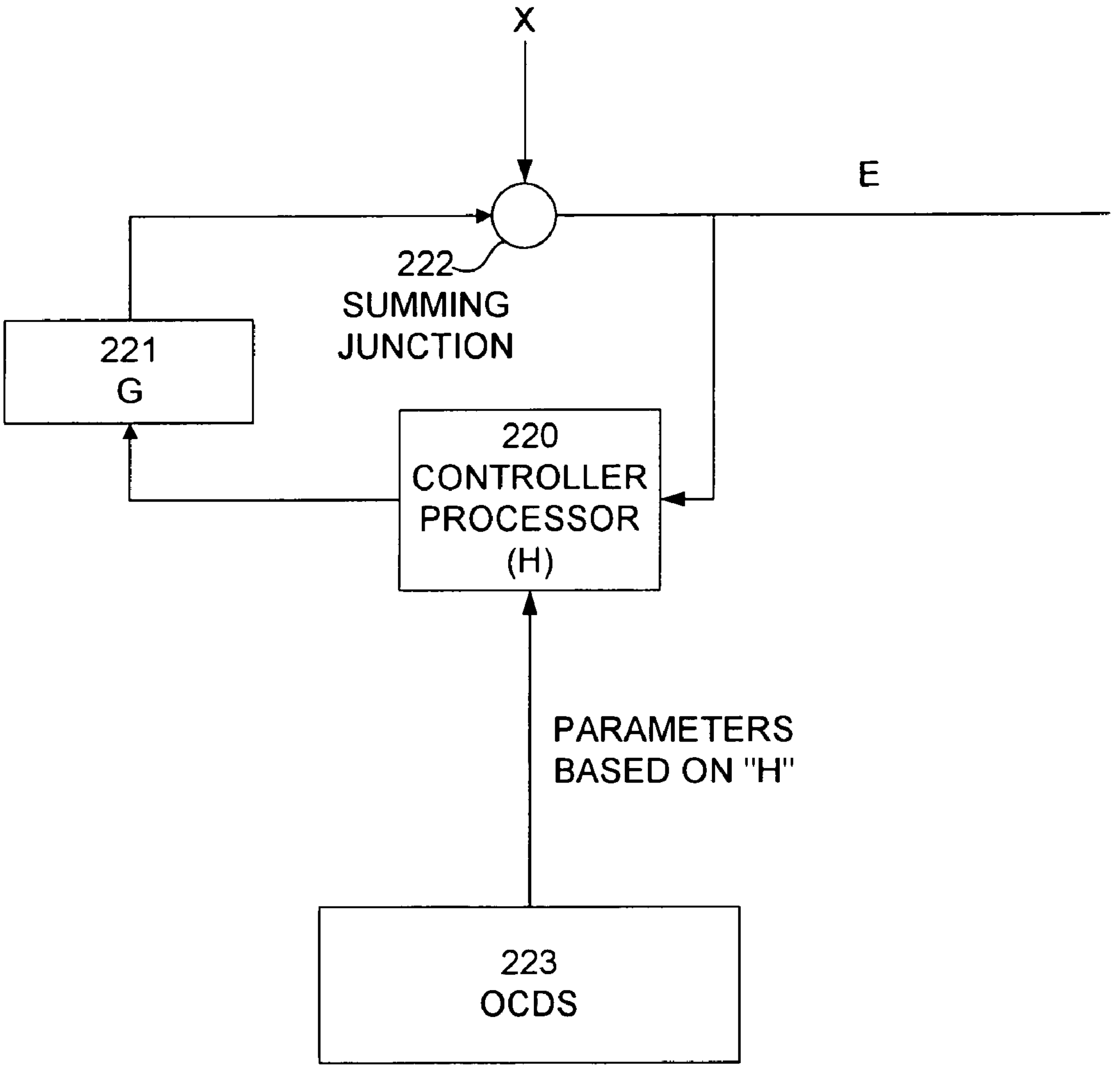
FIG. 9 illustrates a real time implementation of a controller designed in accordance with embodiments of the present invention.

FIG. 9 illustrates a real time implementation of a controller designed in accordance with embodiments of the present invention. Referring to FIG. 9, a controller design is copied from an OCDS 223 to a controller processor 220. The signal x is the disturbance that reaches the summing junction 222 (i.e, see sound sensor, FIG. 2, 125) that is part of the active noise reduction loop. It is important to note that this is different from the metric based signal that was used as part of the controller design procedure. The plant 221 remains the same for the individual that the specific controller was designed for and is generally repeatable for each donning of the hearing protector. The controller design is collected from the OCDS 223 and copied into the controller processor 220 for implementation. The controller processor may be analog, digital, or some combination thereof, that allows implementation of a linear filter. Thus, the controller design comprises a set of parameters that implement a transfer function "H" in the selected controller processor.

The resulting performance minimizes the metric that was used during the design process, which does not necessarily correspond to a minimization of e in FIG. 9, but will result in improved hearing protection tailored to be the best possible for a specific individual in a specific noise field. This is distinct from traditional active noise reduction controller designs for hearing protectors that focus on low frequency control below 1 kHz that rarely impact the A-weighted, passive controlled metric that is minimized by embodiments of the present invention.

Figure 7:
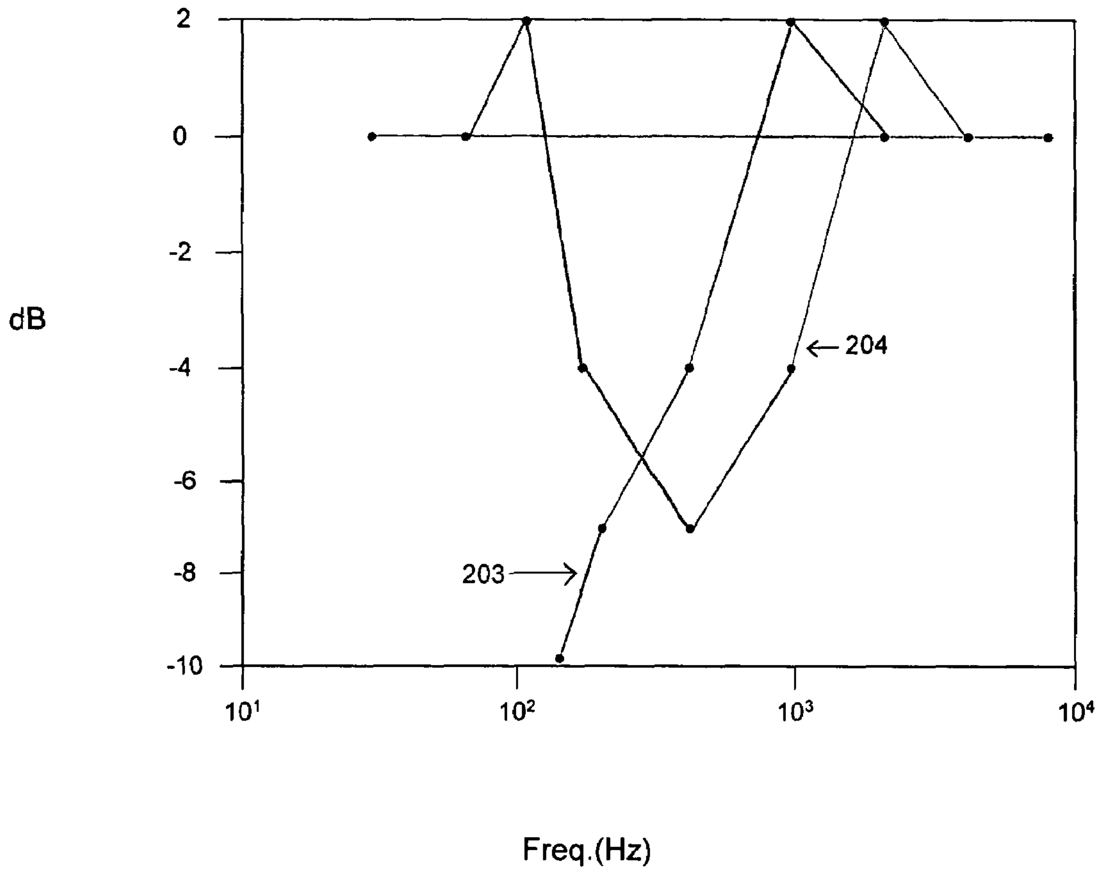
FIG. 7 illustrates the attenuation performance of a controller based on prior art ANR designs and the attenuation performance of a controller designed according to embodiments of the present invention.

FIG. 7 illustrates the attenuation performance of a controller based on prior art ANR designs and the attenuation performance of a controller designed according to embodiments of the present invention. Referring to FIG. 7, trace 203 (marked by triangles) illustrates typical active noise reduction performance for commercially available ANR headsets. Excellent attenuation performance is often achieved below 500 Hz with steadily decreasing performance often leading to amplification by 1-2 kHz (note that negative dB values indicate attenuation and positive indicate amplification). Applying this traditional active noise control approach to the 202 spectrum of FIG. 6 (also represented in FIG. 8 as trace 205), trace 206 results. The overall dB(A) SPL of spectrum 206 is 97.3 dB(A).

Figure 8:
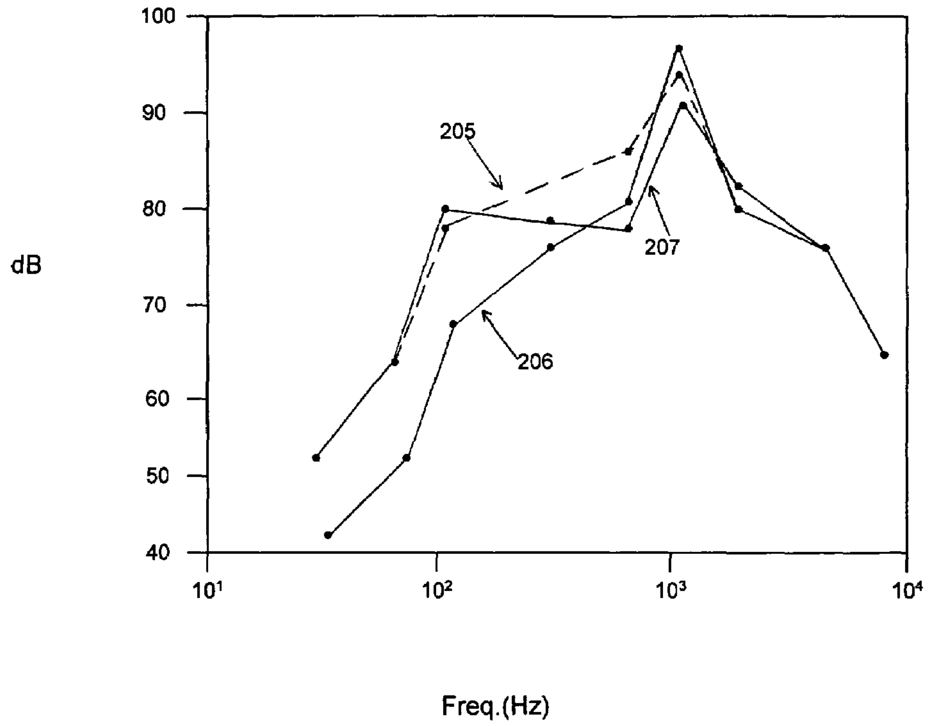
FIG. 8 illustrates the performance benefits in terms of the overall A-weighted dB SPL metric of a controller designed according to embodiments of the present invention compared to the controlled spectrum of the prior art.

Applying the control design procedure described herein and accounting for all elements of the design as presented, the active control performance of trace 204 results. FIG. 8 illustrates the performance benefits in terms of the overall A-weighted dB SPL metric of the controller of trace 204 designed according to embodiments of the present invention. Referring to FIG. 8, applying this controller design (204) to the passively controlled spectrum of 205, spectrum 207 results. Examining the overall A-weighted SPL level of this design yields 92.5 dB(A) SPL; an improvement over traditional methods of 4.8 dB overall.

Figure 4:
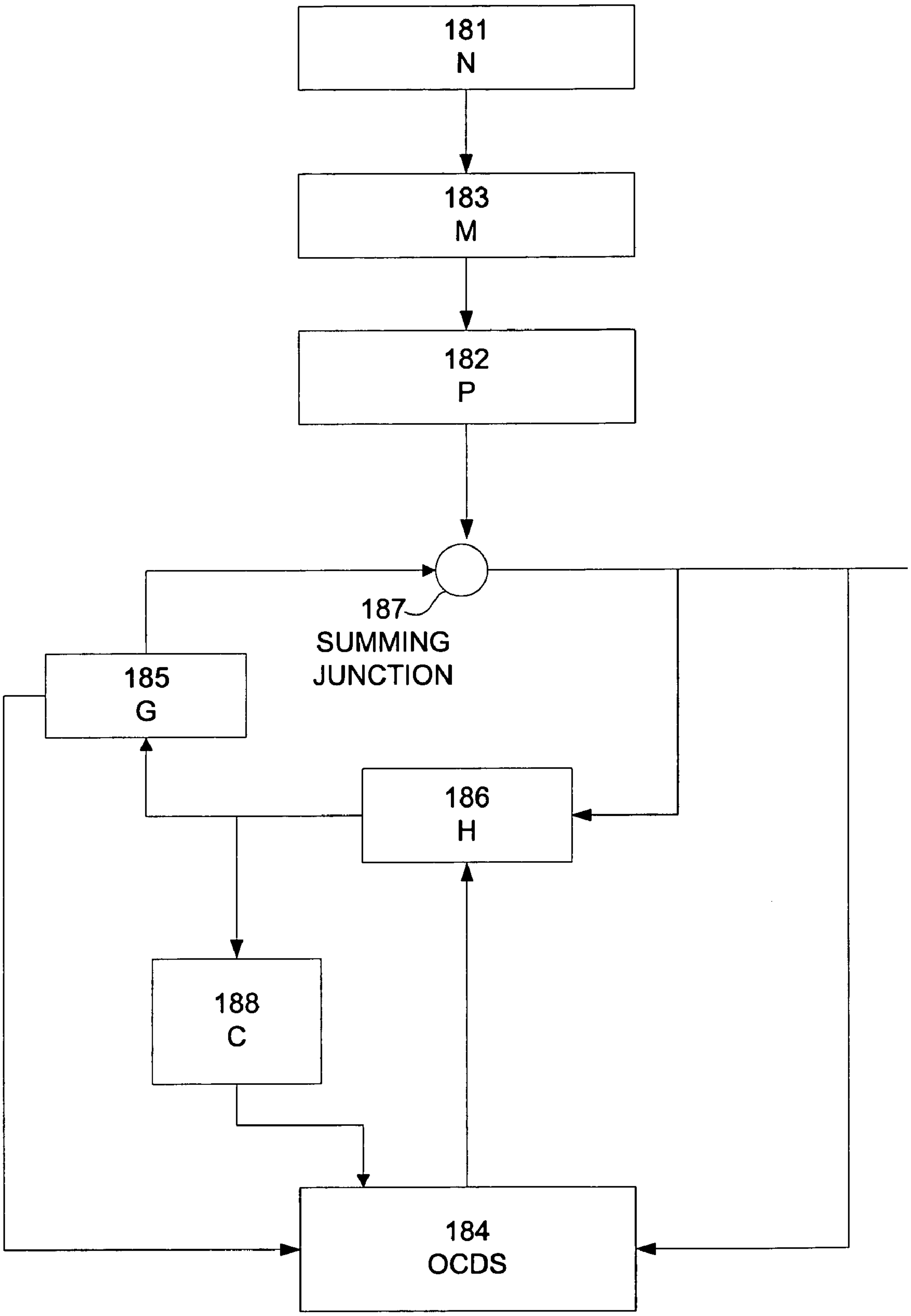
FIG. 4 illustrates the logical components of an OCDS according to other embodiment of the present invention.

FIG. 4 illustrates the logical components of an OCDS according to other embodiments of the present invention. This embodiment of an OCDS differs from that illustrated in FIG. 3 by the inclusion of C 188 as part of the control design procedure. C 188 represents a control signal weighting filter shape that factors into the new cost:

$$w=Cu.$$

In FIG. 4, C 188 represents a weighting filter that filters the control signal that will drive the plant. Quite often the control signal "u" required to drive the plant to achieve cost minimization is too great in magnitude for the actuator to accommodate. This is particularly true for hearing protector designs in high ambient noise fields where small actuators are required to deliver high sound levels. The OCDS 184 in this embodiment of the present invention limits the amplitude of u based on the performance limitations presented by G 185 by using the shape of C 188. C 188 is designed based on the specific hearing protector and is a function of all of the prior design criteria:

$$C(\omega)=f(G(\omega), N(\omega), M(\omega), P(\omega));$$

wherein ω represents a frequency.

Each of the design criteria included in the creation of C 188 is represented as a function of frequency (ω). Physical actuator performance is accounted for in G 185, while the noise field to be controlled under the desired metric is associated with N 181, M 183, and P 182. For noise reduction applications, C 188 is usually designed as a function of frequency because low frequency sounds are more difficult to generate for smaller acoustic drivers. Emphasis can therefore be placed on the bands that explicitly require control, and de-emphasis can be placed on bands where the actuator cannot provide the required SPL in the target noise field defined by N 181, M 183, and P 182.

OCDS 184 determines the optimal the solution for transfer function "H" 186 by minimizing a cost function of the form:

$$J=E[e^T e+w^T w]$$

Minimizing this cost in the controller design results in a controller that will not "over drive" the acoustic actuator but will also minimize J.

Each person is different in anatomy and physiology. This leads to differences in the "plant" (represented by G 165 in FIG. 3 and G 185 in FIG. 4). These differences also lead to differences in performance of the passive hearing protector and active control performance. Embodiments of the present invention account for each of these differences.

Figure 5:
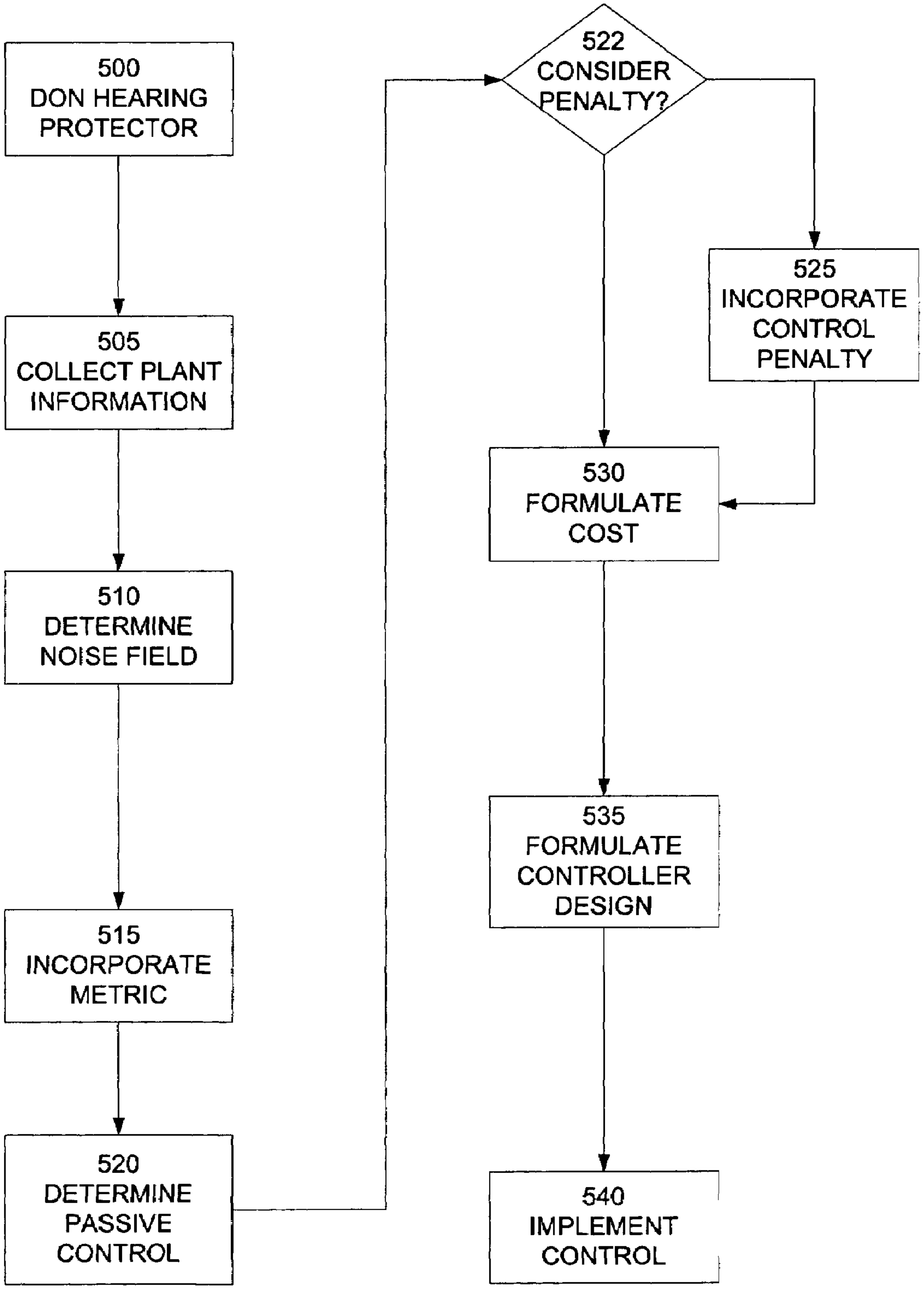
FIG. 5 illustrates a process for designing and manufacturing a controller according to embodiments of the present invention.

FIG. 5 illustrates a process for designing and manufacturing a controller according to embodiments of the present invention. Referring to FIG. 5, a user begins by donning a passive reduction device equipped with active control components 500. If this is a double hearing protector design, both the headset and earplug should be worn at this stage. The "plant" information is then collected on the end user 505, in-situ. Because the plant will differ from person to person, it is important to note that such information should be collected on the final end user. This plant information may take many forms, for example the frequency response, the time response, or the transfer function from the input (actuator) to the output (sensor), depending on the specific control design algorithm to be employed, but will provide an experimental representation of the dynamic system elements described by G above.

Numerous techniques for the determination of the plant information through an automated broadband analysis are known to those skilled in the art of the present invention. One simple automatic method is to excite the plant with broadband white noise and then tune a finite-impulse response (FIR) filter to match the plant output using the least-mean-squares (LMS) algorithm. Another method involves a sine wave sweep over the relevant frequency range to measure the magnitude and phase of the frequency response of the plant. This frequency response may then be fit by an infinite-impulse-response (IIR) or FIR model.

The ambient noise field is determined 510. The spectral shape of the noise field is of primary importance. There are a variety of methods that are anticipated by this invention for determining this parameter of the design. First, the noise field may be measured in advance and included in the control design process through a stored memory location. This may be accomplished by measuring the target noise field with an unweighted microphone and spectrum analyzer, then fitting a spectral shape to the average or instantaneous spectrum, whichever is deemed more relevant for exposure reduction. Storage of the spectral shape can occur in a permanent or semi-permanent manner depending on the final hardware implementation. (This is addressed in greater detail in reference to FIG. 10 below.)

In an embodiment of the present invention, a library of possible noise fields is maintained and the desired noise field is selected from the library. By way of illustration and not as a limitation, the spectrum of a jet noise field may be drastically different from that of a tank, and thus would require a different controller design to achieve the best possible noise attenuation. Providing an in-situ library of noise spectra allow the users, in conjunction with an online controller design method, to have the ability to operate in a variety of noise fields by simply reselecting the operational environment on the controller processor.

In another embodiment of the present invention, an external microphone is included on the hearing protector and the ambient noise field to which the user is exposed is measured. The moment in time when the noise field is measured may either be controlled through a user interface to the controller design procedure or automated when the microphone senses an important change in spectral content requiring an altered controller design to continue to ensure the best, metric-minimizing performance. Numerous algorithms for computing the spectrum of an observed time series are known to those skilled in the art of the present invention. The simplest involve taking fast Fourier transforms (FFTs) of the sampled data coupled with some form of averaging. Other techniques involve building a model of a noise-shaping filter that reproduces the spectral shape of the observed data when excited by white noise. This process may be performed as triggered by an end user through a switch that interrupts a preprogrammed process on a computing platform, or may be initiated automatically each time the controller is turned on. The implementation of the automated control design process is typically carried out through the programming of software on the computing platform which responds to user input or power on and executes the data collection and design instructions sequentially.

The desired metric is incorporated into the controller design 515. The metric may be determined during the design process depending on the desired application goals. It is widely accepted that the A-weighted SPL level is an indicator of the potential for noise exposure related hearing loss. Therefore, for hearing-protector designs, this metric is preferably used to ensure optimized hearing protection performance. Other metrics may also be relevant for different applications including C-weighting, or loudness. In this case the desired metric may be stored in a memory location on the controller processor until the design procedure is carried out. Physical memory locations for the metric, as with the disturbance field, also allow for the availability of multiple metrics in the design process, if desired. The metric information is then retrieved during the controller design process.

The passive control performance of the sound reduction device is incorporated into the design 520. In one embodiment of the present invention, the performance may be determined in advance for a single individual using a REAT or MIRE technique and the attenuation can be applied to the design as described above. This requires a special certification and, while potentially costly and time consuming, has accurate results for the specific individual. In an alternate embodiment of the present invention, the passive sound reduction device is tested on a group of individuals and either the mean attenuation data can be used, or the standard deviation may also be incorporated to form a more conservative estimation of the passive protection. This technique, while also valid, is less accurate for each individual, since the exact performance for that individual is not known and is only approximated by a representative mean value. Both methods have obvious advantages and disadvantages, but the results from either data collection technique are stored in a separate memory location on the target controller processor and used during the controller design process.

In still another embodiment of the present invention, the passive performance is determined by measuring a difference between an external and internal microphone to provide a quantitative insertion loss as a function of frequency in any ambient noise field. This process is similar to the system identification performed on the plant discussed above and can be automated or performed manually by the end user or system designer. This technique for insertion loss determination of a sound reduction device is known in the prior art, but has not been included as an integral part of the design of an active controller intended to improve hearing protection. It is also notable that using an external microphone on the hearing protector design will facilitate both the in-situ disturbance spectrum data collection and the passive insertion loss simultaneously.

Once M, N, and P are determined, a decision is made whether to account for a cost weighting (or control penalty) factor 522. If the control penalty factor to be taken into account, it is included in design process 525 and the process continues with a cost determination at 530. If the control weighting, C, is required to protect a sensitive actuator, it should also be included in the cost 525. The control weighting could be determined by the system designer in advance based primarily on the actuator power handling limitations. Information about the noise field, passive performance, and plant information could also be included in the control weighting to limit or emphasize certain frequency bands of control. As before, that information may be stored on the controller processor for retrieval during the control design process. However, additional information that may govern the selection of C, such as the ambient noise field, may be determined in-situ. If the control penalty is not taken into account, the cost determination is made 530 without using the control penalty factor. Either cost function described above represents a valid approach prescribed by this invention.

A controller design is then determined 535. In an embodiment of the present invention, the design is accomplished using the LQG technique to minimize the cost function. Typically the technique utilizes state-space models of all the transfer functions involved to produce an overall control design model. The optimal controller comprises an optimal estimator (Kalman filter) cascaded with an optimal state feedback matrix. The optimal estimator and state feedback gains can be calculated using eigenvector decompositions of an associated Hamiltonian matrix. Other algorithms using polynomial techniques are also well known in the prior art.

This permits a unique solution for the transfer function "H" that minimizes the chosen cost function. This technique also results in a controller design that is stable when implemented in the closed loop and that minimizes the chosen metric. This is distinct from several prior art approaches that do not deal with stability of the closed loop after design. Stability of the closed loop means that when the controller is implemented, no roots of the closed loop characteristic equation (transfer function denominator) are present in the right half of the complex plane. An unstable design would not satisfy the controller design goals because the response would continue to increase over time.

The result of the controller design process is then used independently of the design process in a real-time implementation of the controller on the actual system it was designed for. The controller parameters are copied 540 to the real-time execution portion of the feedback control loop. The automated procedure described above permits frequent redesign of the active controller for any individual, ensuring the best possible performance for that individual in any noise field.

Figure 10:
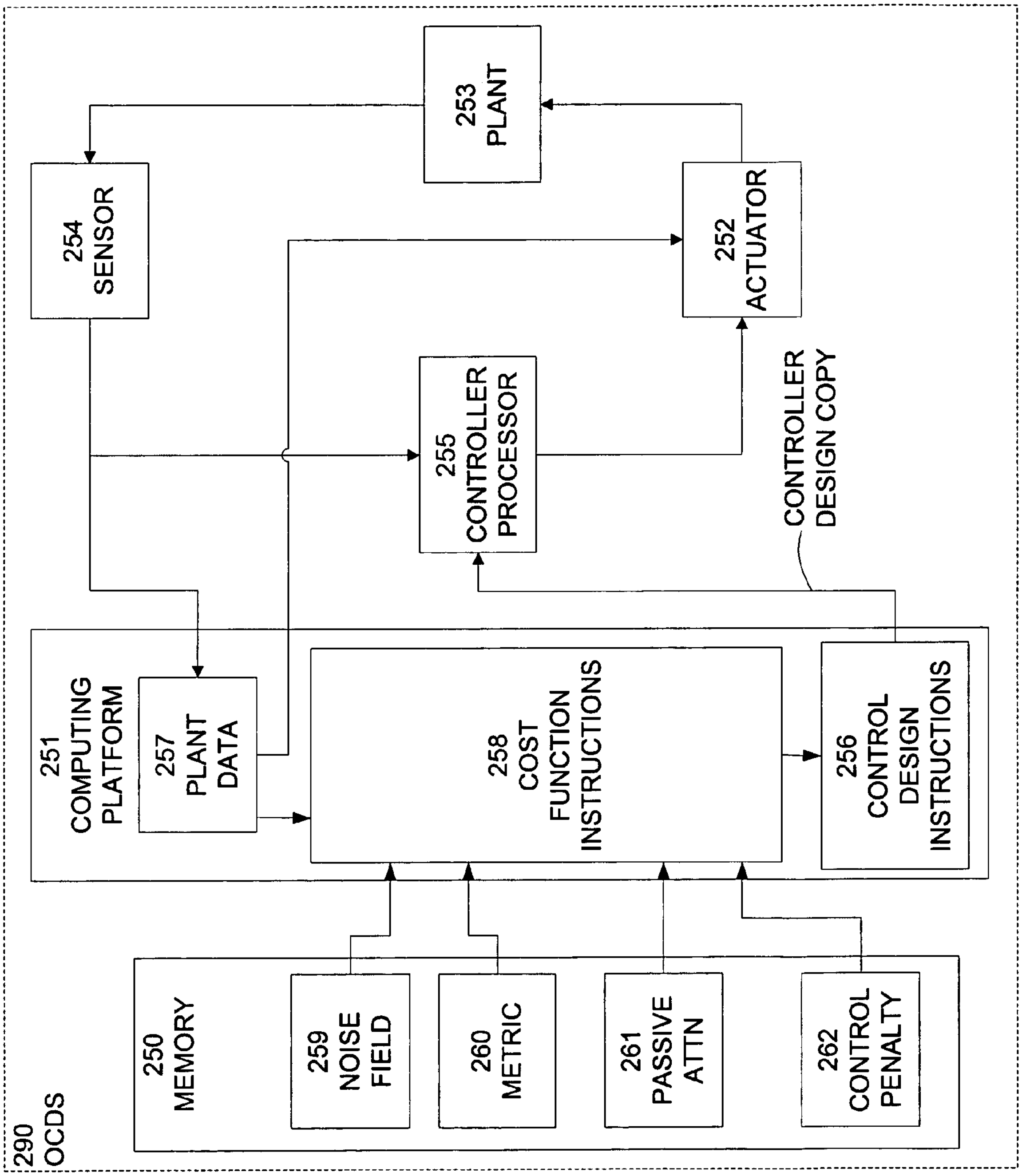
FIG. 10 illustrates a block diagram of a hardware implementation of an OCDS according to embodiments of the present invention.

FIG. 10 illustrates a block diagram of a hardware implementation of an OCDS according to embodiments of the present invention. Referring to FIG. 10, an OCDS 290 comprises a computing platform 251, physical memory 250, and controller processor 255. Computing platform 251 comprises memory locations for the control design instructions 256, the plant data collection 257, and the cost function instructions 258. In an embodiment of the present invention, computing platform 251 comprises a digital signal processor. However the present invention is not so limited. As will be appreciated by those skilled in the art, other computing platforms may be used without departing from the scope of the present invention. By way of illustration and not as a limitation, computing platform 251 may be an FPGA, an ASIC, or a switched capacitor processing agent. Computing platform 251 may further comprise an IIR filter or an FIR filter.

Physical memory 250 comprises memory locations for the noise field 259, metric 260, passive attenuation 261, and control penalty 262. As will be appreciated by those skilled in the art, physical memory 250 may be implemented in RAM, EPROM, flash or some other type of permanent or semi-permanent memory storage media without departing from the scope of the present invention. Actuator 252, plant 253, and sensor 254 are logical components of the hearing protector for which a transfer function "H" (not illustrated) is designed.

As described above, there are several methods whereby each one of these parameters might be collected and placed into their corresponding memory location. The memory 250 is physically connected to the computing platform 251 so the processor may access the memory storage locations during controller design. Within the computing platform 251, there are at least two distinct operational states: offline and real-time. In the offline state the plant data 253 may be collected and stored in memory location 257 by driving the actuator 252 and measuring the sensor 254. The cost may then be determined according to the cost function instructions 258 from the plant data and stored memory locations as appropriate. Once the cost is determined, the control design instructions 256 are performed to minimize the cost. This procedure results in a controller design that is copied to controller processor 255. The controller design comprises a set of parameters that implement a transfer function "H" in the selected controller processor 255. The controller design instructions maybe carried out in the real-time mode or the off-line mode. In the real-time mode, the controller processor 255 reads the sensor 254 and delivers the control signal to the actuator 252 to control the plant 253. The physical plant representation of the application of these elements is shown in FIGS. 1 and 2, depending on the type of hearing protector design that is being used.

The computing platform may also be programmed to operate in alternative states according embodiments of the present invention. In one embodiment of the present invention, the computing platform samples the ambient noise field. This state results in a disturbance spectrum for the target ambient environment and is stored as part of the disturbance spectrum library. In yet another embodiment of the present invention, the computing platform measures the passive noise control performance while the hearing protector is on the user. This information is stored in the memory as the passive noise control performance for that individual. As will be apparent to those skilled in the art, the OCDS may be programmed to operate in various states without departing from the scope of the present invention.

In still another embodiment of the present invention, the entire design and implementation process is automated. In this embodiment, process comprises: 1) power on, 2) collect external data, 3) retrieve stored information from memory, 4) compute cost, 5) design controller transfer function, 6) determine controller parameters to implement the transfer function in the selected controller processor and copy controller parameters to real time control loop, 7) enable real time control loop and store controller. Alternative states may also be realized within the scope of this invention. For example, the "power on" state could be replaced with "user request" which may be tied to a pushbutton that enables an interrupt in the real time process. Such an interrupt would then initiate the rest of the automated design process. Additionally, a measured change in the spectral content of the noise field could also trigger the need to redesign the controller to maximize performance.

A system and method for optimized active controller design in an ANR system has now been described. It will also be understood that the invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the" is not to be construed as limiting the element to the singular.

What is claimed is:

1. A method for customizing a transfer function H for providing active noise reduction tailored to a user of a sound reduction device:

determining an ambient noise field "N" over a spectral segment;

selecting a design metric "M" indicative of a noise reduction objective for the sound reduction device;

determining a measure of the passive performance "P" of the sound reduction device;

determining a measure of the acoustic dynamic response "G" of a user of the sound reduction device to a control signal; and customizing a transfer function "H" for the user based on "N", "P" and "G" by minimizing a cost function of the form J=E[$e^T$ e], wherein $$e = \left[\frac{NMP}{1 + GH}\right]n$$

represents the shaped signal whose average power J is equivalent to the chosen metric M for the user's plant G in the noise field N and passive control P, wherein "H" is tailored for the user of the controller processor;

receiving the customized transfer function "H" at the controller processor; and implementing the customized transfer function "H" in a feedback control loop to achieve the noise reduction objective for the user.

2. The method for determining a transfer function H for providing active noise reduction tailored to a user of a sound reduction device of claim 1, wherein selecting a design metric indicative of a noise reduction objective comprises selecting a design metric from the group consisting of a calculation of the amplitude-weighted sound pressure level, C-weighted sound pressure level, and loudness.

3. The method for determining a transfer function H for providing active noise reduction tailored to a user of a sound reduction device of claim 1, wherein selecting a design metric indicative of a noise reduction objective comprises selecting a design metric indicative of hearing protection.

4. The method for determining a transfer function H for providing active noise reduction tailored to a user of a sound reduction device claim 1, wherein selecting a design metric indicative of a noise reduction objective comprises selecting a design metric from a library of design metrics.

5. The method for determining a transfer function H for providing active noise reduction tailored to a user of a sound reduction device of claim 1, wherein determining an ambient noise field "N" over a spectral segment comprises selecting an ambient noise field "N" from a library of noise fields.

6. The method for determining a transfer function H for providing active noise reduction tailored to a user of a sound reduction device of claim 1, wherein the method further comprises optimizing the transfer function "H".

7. A configurable controller for an active sound reduction device comprising a controller processor adapted to implement a transfer function "H" produced according to the method of claim 4.

8. A configurable controller for an active sound reduction device comprising a controller processor adapted to implement transfer function "H" produced according to the method of claim 1.

9. The method for determining a transfer function H for providing active noise reduction tailored to a user of a sound reduction device of claim 1, further comprising:

means for determining whether a change has occurred in an ambient noise field "N" over a spectral segment used to determine the transfer function "H";

means for determining whether a change has occurred in a measure of the passive performance "P" of a hearing protection device used to determine the transfer function "H";

means for determining whether a change has occurred in a measure of the acoustic dynamic response "G" of a user of the hearing protection device to a control signal used to determine the transfer function "H"; and applying means for producing a revised transfer function "$H_R$" if a change is detected in any one of N, P, and G.

10. The method for determining a transfer function H for providing active noise reduction tailored to a user of a sound reduction device of claim 9 further comprising:

means for selecting a design metric indicative of a noise reduction objective;

means for determining whether the selected design metric differs from the design metric used to determine the transfer function "H"; and applying means for producing a revised transfer function "$H_R$" if the selected design metric differs from the from the design metric used to determine the transfer function "H".

* * * * *